(12) United States Patent
Blyth et al.

(10) Patent No.: US 8,168,221 B2
(45) Date of Patent: May 1, 2012

(54) COMPOSITION 064

(75) Inventors: John David Blyth, Macclesfield (GB); Andrew John Day, Macclesfield (GB); Kieran James Lennon, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 326 days.

(21) Appl. No.: 12/249,157

(22) Filed: Oct. 10, 2008

(65) Prior Publication Data

US 2009/0099203 A1      Apr. 16, 2009

Related U.S. Application Data

(60) Provisional application No. 60/979,736, filed on Oct. 12, 2007, provisional application No. 61/089,118, filed on Aug. 15, 2008.

(51) Int. Cl.
*A61K 9/20* (2006.01)

(52) U.S. Cl. ..................................................... 424/464

(58) Field of Classification Search .................. None
See application file for complete search history.

(56) References Cited

U.S. PATENT DOCUMENTS

| | | | | |
|---|---|---|---|---|
| 3,674,794 | A * | 7/1972 | Mizzoni et al. | 546/293 |
| 6,248,767 | B1 | 6/2001 | Blok et al. | |
| 2006/0030581 | A1* | 2/2006 | DeBusi et al. | 514/300 |
| 2006/0122180 | A1 | 6/2006 | Boyle et al. | |

FOREIGN PATENT DOCUMENTS

| | | | |
|---|---|---|---|
| WO | 96/40681 | A1 | 12/1996 |
| WO | 03/041705 | A1 | 5/2003 |
| WO | WO 03041705 | A1 * | 5/2003 |
| WO | 2004/018044 | A2 | 3/2004 |
| WO | WO 2004018044 | A2 * | 3/2004 |
| WO | 2005/105096 | A2 | 11/2005 |
| WO | 2009/047565 | A2 | 4/2009 |

OTHER PUBLICATIONS

J. A. Westerhuis, P. de Haanb, J. Zwinkels, W. T. Jansen, P. J. M. Coenegracht and C. F. Lerk. Optimisation of the composition and production of mannitol/microcrystalline cellulose tablets. International Journal of Pharmaceutics, vol. 143, Issue 2, 8 U Nov. 1996, pp. 151-162.*

Carducci et al. 'Targeting Bone Metastasis in Prostate Cancer with Endothelin Receptor Antagonists' Clinical Cancer Research (2006); vol. 12; pp. 6296s-6300s.

Rosano et al. 'ZD4054, A Potent Endothelin Receptor A Antagonist, Inhibits Ovarian Carcinoma Cell Proliferation' Molecular Pathology and Ultrastructure Laboratory, and Immunology Laboratory, Regina Elena Cancer Institute, Rome, Italy (2006); pp. 1132-1135.

EMEA/410/01 Rev. 2 "Note for Guidance on Minimising the Risk of Transmitting Animal Spongiform Encephalopathy Agents via Human and Veterinary Medicinal Products". Official Journal of the European Union (adopted by CPMP/CVMP Oct. 2003).

ICH Guideline Q6A: "Specifications: Test Procedures and Acceptance Criteria for New Drug Substances and New Drug Products: Chemical Substances" Published in the Federal Register, Dec. 29, 2000; vol. 65; No. 251; notices; pp. 83041-83063.

Callahan et al. "Equilibrium Moisture Content of Pharmaceutical Excipients". Drug Development and Industrial Pharmacy (1982); vol. 3; No. 3; pp. 355-369.

Westerhuis et al. "Optimisation of the Composition and Production of Mannitol/Microcrystalline Cellulose Tablets.", International Journal of Pharmaceutics (1996); vol. 143; pp. 151-162.

Nelson et al. "Identification of Endothelin-1 in the Pathophysiology of Metastatic Adenocarcinoma of the Prostate". Nature Medicine (1995); vol. 1; No. 9; pp. 944-949.

Nelson et al. "Endothelin-1 Production and Decreased Endothelin B Receptor Expression in Advanced Prostate Cancer". Cancer Research (1996); vol. 56; pp. 663-668.

Carstensen et al. Solid Pharmaceutics: Mechanical Properties and Rate Phenomena, Academic Press, NY (1980); pp. 200-203.

Sheth et al. "Pharmaceutical Dosage Forms: Tablets" Marcel Dekker, Inc. (1980); vol. 1; pp. 109-185.

English translation of a third party opposition from Chilean Patent Application No. 03022-2008, which is a counterpart of the present U.S. patent application. The foreign language version of the opposition was received from foreign counsel on Dec. 6, 2011.

* cited by examiner

*Primary Examiner* — Robert A Wax
*Assistant Examiner* — Olga V Tcherkasskaya

(57) ABSTRACT

A pharmaceutical composition which comprises N-(3-methoxy-5-methylpyrazin-2-yl)-2-(4-[1,3,4-oxadiazol-2-yl]phenyl)pyridine-3-sulphonamide with mannitol and/or 5 microcrystalline cellulose is described.

17 Claims, No Drawings

COMPOSITION 064

RELATED APPLICATIONS

This application claims the benefit under 35 U.S.C. 119(e) of U.S. Provisional Application No. 60/979,736, filed Oct. 12, 2007 and U.S. Provisional Application No. 61/089,118, filed Aug. 15, 2008. The entire teaching of U.S. 60/979,736 and U.S. 61/089,118 are incorporated herein by reference.

FIELD OF THE INVENTION

The present application refers to a novel pharmaceutical composition of N-(3-methoxy-5-methylpyrazin-2-yl)-2-(4-[1,3,4-oxadiazol-2-yl]phenyl)pyridine-3-sulphonamide (hereafter "Compound (I)"). More specifically the invention relates to a pharmaceutical composition comprising Compound (I) with mannitol and/or microcrystalline cellulose, and to methods of treating cancer in a warm blooded animal such as man using this composition.

BACKGROUND OF THE INVENTION

Compound (I) is an endothelin antagonist. The endothelins are a family of endogenous 21 amino acid peptides comprising three isoforms, endothelin-1 (ET-1), endothelin-2 and endothelin-3. The endothelins are formed by cleavage of the $Trp^{21}$-$Val^{22}$ bond of their corresponding proendothelins by an endothelin converting enzyme. The endothelins are among the most potent vasoconstrictors known and have a characteristic long duration of action. They exhibit a wide range of other activities including cell proliferation and mitogenesis, extravasation and chemotaxis, and also interact with a number of other vasoactive agents.

The endothelins are released from a range of tissue and cell sources including vascular endothelium, vascular smooth muscle, kidney, liver, uterus, airways, intestine and leukocytes. Release can be stimulated by hypoxia, shear stress, physical injury and a wide range of hormones and cytokines. Elevated endothelin levels have been found in a number of disease states in man including cancers.

Recently, endothelin A receptor antagonists have been identified as potentially of value in the treatment of cancer (Cancer Research, 56, 663-668, Feb. 15, 1996 and Nature Medicine, Volume 1, Number 9, September 1999, 944-949).

Cancer affects an estimated 10 million people worldwide. This figure includes incidence, prevalence and mortality. More than 4.4 million cancer cases are reported from Asia, including 2.5 million cases from Eastern Asia, which has the highest rate of incidence in the world. By comparison, Europe has 2.8 million cases, North America 1.4 million cases, and Africa 627,000 cases.

In the UK and US, for example, more than one in three people will develop cancer at some point in their life. Cancer mortality in the U.S. is estimated to account for about 600,000 a year, about one in every four deaths, second only to heart disease in percent of all deaths, and second to accidents as a cause of death of children 1-14 years of age. The estimated cancer incidence in the U.S. is now about 1,380,000 new cases annually, exclusive of about 900,000 cases of non-melanotic (basal and squamous cell) skin cancer.

Cancer is also a major cause of morbidity in the UK with nearly 260,000 new cases (excluding non-melanoma skin cancer) registered in 1997. Cancer is a disease that affects mainly older people, with 65% of cases occurring in those over 65. Since the average life expectancy in the UK has almost doubled since the mid nineteenth century, the population at risk of cancer has grown. Death rates from other causes of death, such as heart disease, have fallen in recent years while deaths from cancer have remained relatively stable. The result is that 1 in 3 people will be diagnosed with cancer during their lifetime and 1 in 4 people will die from cancer. In people under the age of 75, deaths from cancer outnumber deaths from diseases of the circulatory system, including ischaemic heart disease and stroke. In 2000, there were 151,200 deaths from cancer. Over one fifth (22 per cent) of these were from lung cancer, and a quarter (26 per cent) from cancers of the large bowel, breast and prostate.

Worldwide, the incidence and mortality rates of certain types of cancer (of stomach, breast, prostate, skin, and so on) have wide geographical differences which are attributed to racial, cultural, and especially environmental influences. There are over 200 different types of cancer but the four major types, lung, breast, prostate and colorectal, account for over half of all cases diagnosed in the UK and US. Prostate cancer is the fourth most common malignancy among men worldwide, with an estimated 400,000 new cases diagnosed annually, accounting for 3.9 percent of all new cancer cases.

Current options for treating cancers include surgical resection, external beam radiation therapy and/or systemic chemotherapy. These are partially successful in some forms of cancer, but are not successful in others. There is a clear need for new therapeutic treatments.

Compound (I) is exemplified and described in WO96/40681 as Example 36. WO96/40681 claims the endothelin receptors described therein for the treatment of cardiovascular diseases. The use of Compound (I) in the treatment of cancers and pain is described in WO04/018044.

Compound (I) has the following structure:

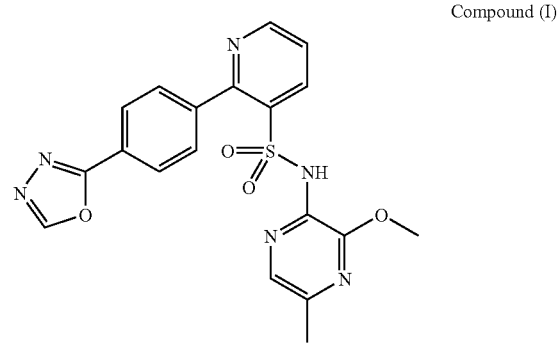

Compound (I)

and is also known as zibotentan.

In WO04/018044 an endothelin human receptor binding assay is described. The $pIC_{50}$ (negative log of the concentration of compound required to displace 50% of the ligand) for Compound (I) at the $ET_A$ receptor was 8.27 [8.23-8.32] (n=4). Compound (I) is thus an excellent endothelin antagonist.

WO96/40681 discloses in general terms, certain pharmaceutically compositions that may be used to formulate compounds of the invention described therein (for example see Example 71).

WO04/018044 describes a lactose formulation of Compound (I):

Compound (I);
Lactose monohydrate (filler);
Croscarmellose sodium (disintegrant);
Povidone (binder);
Magnesium stearate (lubricant);
Hypromellose (film coat component);
Polyethylene glycol 300 (film coat component); and
Titanium dioxide (film coat component).

This tablet formulation, based on a lactose monohydrate filler and with a white film coat, was developed for use in Phase I and II clinical studies, but proved unsuitable for use in late-stage development because:

the tablets were prone to capping and edge-damage;
the active ingredient was subject to hydrolytic degradation;
the active ingredient was subject to degradation on exposure to light; and
strict controls must be applied to lactose monohydrate to minimize the risk of TSE (Transmissible Spongiform Encephalopathy) transmission, as described in EMEA/410/01 Rev. 2 Note for Guidance on Minimising the Risk of Transmitting Animal Spongiform Encephalopathy Agents via Human and Veterinary Medicinal Products, (Adopted by CPMP/CVMP October 2003).

The term 'capping' means the complete or partial separation of a saucer-shaped disc from the top or bottom surface of a tablet during compression of the material to form a tablet or during subsequent processes and/or handling. Capping is described in Carstensen, J. T., Solid pharmaceutics: mechanical properties and rate phenomena, Academic press, New York (1980) and in Sheth et al., Pharmaceutical dosage forms: Tablets. Vol 1. Ed Liebermann and Lachmann, Pub. Marcel Dekker, New York (1980).

The term 'edge damage' means loss of material from the regions where the tablet surfaces intersect, during compression of the material to form a tablet or during subsequent processes and/or handling.

Compound (I) is subject to hydrolytic degradation at low and high pH, the principal degradation product being Compound (I) formyl hydrazide:

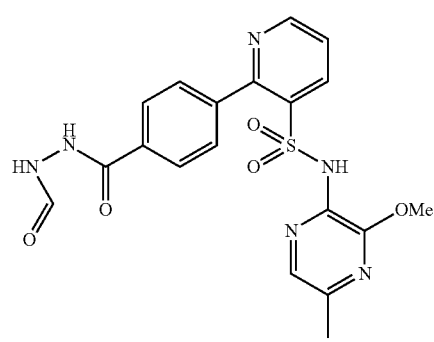

formyl hydrazide

Over time, Compound (I) formyl hydrazide may further degrade to form Compound (I) hydrazide:

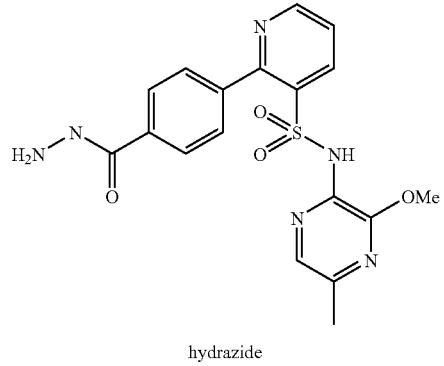

hydrazide

Compound (I) formyl hydrazide and Compound (I) hydrazide are also formed under hydrolytic conditions upon exposure to light. In the solid state, the principal degradation product following exposure to light is Compound (I) des pyrazine:

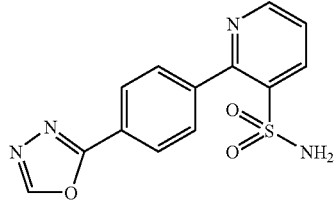

des pyrazine

In one aspect there is provided Compound (I) formyl hydrazide.

In one aspect there is provided Compound (I) hydrazide.

In one aspect there is provided Compound (I) des pyrazine.

In addition to the above, tablets need to possess sufficient hardness or sufficient mechanical strength, which will prevent a compact from becoming damaged during subsequent processing or transport. This is related to the size of the tablet and when measured in kiloponds (kp) is typically <15 kp. Suitably an immediate release tablet has a hardness in the range of from 5 to 20 kp, for example about 10 kp.

Friability is the phenomenon whereby tablet surfaces are damaged and/or show evidence of cracking or breakage when subjected to mechanical agitation (e.g. during processing, handling or transportation).

Disintegration is the process whereby a tablet breaks down into its constituent particles when in contact with a fluid. Disintegration is a desirable property for an immediate release tablet as this leads to an increase in surface area and hence may lead to an increased rate of dissolution. In vivo, disintegration should occur as soon as possible following administration to the gastrointestinal tract, for example within 15 minutes. For immediate release tablets a suitable disintegration time under the standard United States Pharmacopoeia (USP) disintegration method is in the range of for example about 3 to 15 minutes and typically 5 to 8 minutes. Generally in the in-vivo setting immediate release tablets are not designed to exhibit significant disintegration in the oral cavity. Rather the disintegration occurs in the upper GI tract, predominantly in the stomach. An immediate release tablet formulation may include a disintegrant in order to promote tablet disintegration.

Immediate release allows the drug to dissolve in the gastrointestinal contents, with no intention of delaying or prolonging the dissolution or absorption of the drug (ICH Guideline Q6A: "Specifications: Test Procedures and Acceptance Criteria for New Drug Substances and New Drug Products: Chemical Substances" Published in the Federal Register, Dec. 29, 2000, Volume 65, Number 251, Notices, Page 83041-83063).

Dissolution is the process whereby the active substance is released from a tablet following exposure to a fluid, such that the drug becomes dissolved in the fluid. For testing purposes the fluid is usually chosen to simulate conditions within the gastrointestinal tract, and is most usually an aqueous medium at low or neutral pH. For an immediate release tablet dissolution should be rapid, for example should be substantially complete within a period of 45 minutes following exposure to fluid under standard test conditions. For example, dissolution measured according to the general procedure of the USP using Apparatus 2 with 900 mL of 0.1 M Phosphate buffer at pH 7.8 as dissolution medium and a stirrer speed of 50 rpm. Typical USP acceptance criteria for dissolution from an immediate release tablet for the amount of active ingredient dissolved is typically 75 to 80% by weight of the active ingredient in the tablet. Tablet hardness, disintegration time and dissolution rate may be inter-related in that an increase in hardness may lead to an increase in disintegration time and hence a decrease in dissolution rate. The target profile for an immediate release tablet is one with sufficient hardness to prevent friability problems, but which disintegrates and dissolves rapidly within the gastrointestinal tract. An assessment of suitability may commence with the determination of tablet hardness followed, when appropriate, by more complex tests including disintegration testing and/or dissolution testing.

In an attempt to resolve the issues with the lactose formulation containing Compound (I) described above, alternative fillers for a composition comprising a Compound (I) were investigated. Acceptable results gave maximum total impurities <1.5% and minimum dissolution of 80% for dissolution (as described in the Experimental Section herein below) over 45 minutes.

Tablet cores prepared comprising Compound (I) with calcium phosphate dihydrate (as defined in the European Pharmacopia (PhEur)) (Calipharm™ D) as the filler were particularly poor with regard to dissolution performance. Similarly the use of magnesium carbonate, heavy (as defined in the PhEur) as the filler led to tablet cores which performed poorly with regard to impurity levels.

Microcrystalline cellulose is hygroscopic (see for example: 'Equilibrium moisture content of pharmaceutical excipients' Callahan, J. C., Cleary, G. W., Elefant, M., et al, *Drug Dev Ind Pharm* 1982; 8: 355-369) and moisture pick-up on storage of tablets using that as the filler (leading to hydrolytic degradation of Compound (I)) was expected. However, surprisingly, we have found that certain tablet compositions containing microcrystalline cellulose as one of the excipients do not result in any undue hydrolytic degradation of Compound (I). Tablet cores comprising Compound (I) with microcrystalline cellulose as the filler together with certain other excipients did not exhibit significant capping or edge damage, gave acceptable results with regard to dissolution performance, and did not exhibit significant chemical degradation when protected from light. Some degradation was observed following exposure to light, but the tablets in this study were not film coated.

Tablet cores prepared comprising Compound (I) with mannitol as the filler gave acceptable results in hardness experiments even though earlier prepared placebo tablet cores (no Compound (I)) with a mannitol-based formulation had showed that these tablet cores were subject to hardening on storage leading to increased disintegration times. These mannitol-based tablet cores were also acceptable with regard to dissolution performance; and although when stored at high temperature and humidity a deterioration in dissolution performance was observed for one of the formulations, this effect was thought to be attributable to the disintegrant and/or binder present in the formulation and was not considered significant with respect to the criteria used to assess dissolution performance.

Tablet cores with and without Compound (I) with both mannitol and microcrystalline cellulose as the fillers were acceptable with regard to both hardness over time and physical stability. Tablet cores containing Compound (I) with both mannitol and microcrystalline cellulose as the fillers also did not exhibit undue hydrolytic degradation despite the hygroscopic nature of microcrystalline cellulose, and were acceptable with regard to dissolution.

The formulations of Compound (I) comprising mannitol and/or microcrystalline cellulose have one or more advantageous properties selected from:
  the formulation uses excipients which are not subject to strict controls to minimise the possibility of TSE transmission;
  when the formulation is in the form of a tablet the formulation is physically stable in that it exhibits one or more of the following properties:
    it is not subject to significant capping/edge damage;
    it shows a reduced tendency to harden on storage;
    it does not absorb significant quantities of water on storage; and
  the formulation is chemically stable in that the levels of hydrolytic degradation of Compound (I) are low.

SUMMARY OF THE INVENTION

Therefore in one aspect of the present invention there is provided a pharmaceutical composition which comprises Compound (I) with mannitol and/or microcrystalline cellulose.

According to a further aspect of the invention there is provided a method of treating cancer which comprises administering an effective amount of a pharmaceutical composition, which comprises Compound (I) with mannitol and/or microcrystalline cellulose, to a warm blooded animal such as man.

DETAILED DESCRIPTION OF THE INVENTION

Herein where "mannitol and/or microcrystalline cellulose" is referred to, in one aspect of the invention this refers to mannitol with no microcrystalline cellulose. In a further aspect of this invention this refers to microcrystalline cellulose and no mannitol. In a further aspect of this invention this refers to both mannitol and microcrystalline cellulose.

In another aspect of the invention there is provided a pharmaceutical composition which comprises Compound (I), mannitol and microcrystalline cellulose, wherein the weight ratio of mannitol:microcrystalline cellulose is from about 10:1 to about 1:2. For example, the weight ratio of mannitol to microcrystalline cellulose is from about 10:1 to about 1:1. In another embodiment the weight ratio of mannitol to microcrystalline cellulose is about 8:1 to about 2:1. In a further embodiment the weight ratio of mannitol to microcrystalline cellulose is from about 7:1 to about 5:1. For example the weight ratio of mannitol to microcrystalline cellulose is about 6:1.

Microcrystalline cellulose refers to "Cellulose, microcrystalline" as described in the European Pharmacopoeia (PhEur). The composition according to the invention may use any microcrystalline cellulose suitable for use in pharmaceutical compositions such as tablets. In one embodiment the grade of microcrystalline cellulose may be defined by specific surface area e.g. −1.21-1.30 $m^2/g$ for the placebo tablets and 1.06-1.12 $m^2/g$ for tablets containing Compound (I). In another embodiment the microcrystalline cellulose has average particle size in the range of from about 40 to about 120 μm, for example about 50 to about 100 μm. In a particular embodiment the microcrystalline cellulose has an average particle size of about 50 μm. In another particular embodiment the microcrystalline cellulose has an average particle size of about 100 μm. Suitably the bulk density of the microcrystalline cellulose is (prior to incorporation into the composition) of about 0.25 to about 0.38 $g/cm^3$. For example in one embodiment the bulk density is about 0.26 to about 0.31 $g/cm^3$. In another embodiment the bulk density is 0.28 to about 0.33 $g/cm^3$. In one embodiment the microcrystalline cellulose is substantially free from moisture prior to incorporation into the composition according to the invention (for example containing less than 3, 2 or 1% by weight water). In another embodiment the microcrystalline cellulose contains about 3 to 6% by weight of water prior to incorporation into the composition, for example about 5%. Microcrystalline cellulose as used herein may also refer to microcrystalline cellulose sold under the trade name Avicel® (ex FMC corp.). In one embodiment the microcrystalline cellulose is Avicel® PH-101. In another embodiment the microcrystalline cellulose is Avicel® PH-102.

Alternative disintegrants were also investigated. The use of croscarmellose sodium (described in the PhEur) as disintegrant was found to yield lower levels of impurities in comparison with crospovidone.

In one aspect the pharmaceutical composition additionally contains one or more disintegrants. In another aspect, the pharmaceutical composition additionally contains one disintegrant. In another aspect, the pharmaceutical composition additionally contains croscarmellose sodium. Any grade of croscarmellose sodium suitable for pharmaceutical formulation may be used, for example Ac-Di-Sol® (FMC Corp.)

In one aspect the pharmaceutical composition additionally contains one or more binders. Suitable binders include, for example, lactose, starches, modified starches, sugars, gum acacia, gum tragacanth, guar gum, pectin, wax binders, methylcellulose, carboxymethylcellulose, hydroxypropyl methylcellulose, hydroxyethyl cellulose, hydroxypropyl cellulose, copolyvidone, gelatine, polyvinylpyrollidone (PVP or Povidone) and sodium alginate. In another aspect, the pharmaceutical composition additionally contains one binder selected from lactose, starches, modified starches, sugars, gum acacia, gum tragacanth, guar gum, pectin, wax binders, methylcellulose, carboxymethylcellulose, hydroxypropyl methylcellulose, hydroxyethyl cellulose, hydroxypropyl cellulose, copolyvidone, gelatine, polyvinylpyrrolidone (Povidone) and sodium alginate. In another aspect, the pharmaceutical composition additionally contains Povidone.

The skilled reader will understand that a component of the tablet can act in more than one capacity. For example in some embodiments microcrystalline cellulose could act as a binder and/or a disintegrant as well as a filler.

Particularly where "Povidone" is referred to this refers to a synthetic water-soluble homopolymer consisting of N-vinyl pyrrolidone (also known as 1-vinyl-2-pyrrolidinone polymers; polyvinlypyrrolidone; polyvidone; or PVP). Various grades of povidone are available of varying molecular weights. The grade of the povidone is often denoted by a K value, which is calculated from dilute solution viscosity measurements, and is used to denote degree of polymerization or molecular size). A low K value indicates a low molecular weight and a high K-value a high molecular weight. For example, grade K-12 povidone has an approximate weight average molecular weight of 4000, K-17 about 10,000, K-26 about 34,000, K30 about 49,000 and K-29/32 about 58,000. In one embodiment of the invention the povidone is grade K30. In another embodiment the povidone is Povidone K29/32 (for example Plasdone™ K29/32). In another embodiment the povidone is Kollidon™ K30.

In one aspect the pharmaceutical composition additionally contains one or more lubricants. Suitable lubricants include, for example, magnesium stearate, stearic acid, palmitic acid, calcium stearate, talc, carnuba wax, hydrogenated vegetable oils, mineral oil, polyethylene glycols and sodium stearyl fumarate. In another aspect, the pharmaceutical composition additionally contains one lubricant selected from magnesium stearate, stearic acid, palmitic acid, calcium stearate, talc, carnuba wax, hydrogenated vegetable oils, mineral oil, polyethylene glycols and sodium stearyl fumarate. In another aspect, the pharmaceutical composition additionally contains magnesium stearate.

In one aspect, the pharmaceutical composition contains from 2 to 40% by weight of Compound (I). For example it contains from 2 to 25% by weight of Compound (I). In one embodiment the composition contains 2 to 20% by weight of Compound (I). In particular it contains 4.5 to 8.5% by weight of Compound (I). Suitably the composition according to the invention, such as a capsule or tablet, contains 10 mg of Compound (I). In another aspect the composition, such as a capsule or tablet, contains 15 mg of Compound (I).

In another aspect, the pharmaceutical composition contains from 50 to 95% by weight of filler. In another aspect the composition contains from 82 to 85% by weight of filler. In particular, it contains 84 to 88% by weight of filler.

In one aspect, the filler is mannitol. In another aspect, the filler is microcrystalline cellulose. In another aspect, the filler is mannitol and microcrystalline cellulose. In one embodiment the composition contains about 65 to 75% by weight of mannitol, for example about 71 to 74% by weight. In another embodiment the composition contains about 10 to 15% by weight of microcrystalline cellulose, for example about 12 to 13% by weight. In particular, the composition contains 12.5 to 16.5% by weight of microcrystalline cellulose. In another embodiment the composition contains from about 65 to 75% by weight of mannitol and about 10 to 15% by weight of microcrystalline cellulose.

In another aspect, the pharmaceutical composition contains from 1 to 5% by weight of disintegrant. In particular, it contains 2.5 to 3.5% by weight of disintegrant.

In another aspect, the pharmaceutical composition contains from 1 to 5% by weight of binder. In particular, it contains 2.5 to 3.5% by weight of binder.

Typically one or more lubricants will be present in an amount from 0.5 to 2.5% by weight, particularly 0.75 to 2% by weight and especially 0.75 to 1.25% by weight.

In one aspect the invention relates to a pharmaceutical composition comprising:

Compound (I) in an amount of 4.5 to 8.5% by weight;
mannitol in an amount of 71 to 76% by weight (for example 71.5 to 75.5% by weight); and
microcrystalline cellulose in an amount of 10.5 to 14.5% by weight.

In another aspect the invention relates to a pharmaceutical composition comprising:
Compound (I) in an amount of 4.5 to 8.5% by weight;
mannitol in an amount of 71 to 76% by weight (for example 71.5 to 75.5% by weight);
microcrystalline cellulose in an amount of 10.5 to 14.5% by weight;
Croscarmellose sodium in an amount of 2.5 to 3.5% by weight;
one or more binders in an amount of 2.5 to 3.5% by weight; and
one or more lubricants in an amount of 0.75 to 2.0% by weight (for example 0.75 to 1.25% by weight.

In another aspect the invention relates to a pharmaceutical composition comprising:
Compound (I) in an amount of 4.5 to 8.5% by weight;
mannitol in an amount of 71 to 76% by weight (for example 71.5 to 75.5% by weight);
microcrystalline cellulose in an amount of 10.5 to 14.5% by weight;
croscarmellose sodium in an amount of 2.5 to 3.5% by weight;
one or more binders in an amount of 2.5 to 3.5% by weight; and
magnesium stearate in an amount of 0.75 to 2.0% by weight (for example 0.75 to 1.25% by weight).

In another aspect the invention relates to a pharmaceutical composition comprising:
Compound (I) in an amount of 4.5 to 8.5% by weight;
mannitol in an amount of 71 to 76% by weight (for example 71.5 to 75.5% by weight);
microcrystalline cellulose in an amount of 10.5 to 14.5% by weight;
croscarmellose sodium in an amount of 2.5 to 3.5% by weight;
Povidone (for example Kollidon™ K-30 or Plasdone™ K29/32) in an amount of 2.5 to 3.5% by weight; and
one or more lubricants in an amount of 0.75 to 2.0% by weight (for example 0.75 to 1.25% by weight.

In another aspect the invention relates to a pharmaceutical composition comprising:
Compound (I) in an amount of 4.5 to 8.5% by weight;
mannitol in an amount of 71 to 76% by weight (for example 71.5 to 75.5% by weight);
microcrystalline cellulose in an amount of 10.5 to 14.5% by weight;
croscarmellose sodium in an amount of 2.5 to 3.5% by weight;
Povidone (for example Kollidon™ K-30 or Plasdone™ K29/32) in an amount of 2.5 to 3.5% by weight; and
magnesium stearate in an amount of 0.75 to 2.0% by weight (for example 0.75 to 1.25% by weight).

As will be realised, where herein compositions are described in terms of % by weight of components of the composition, the sum of the % by weight of all of the components of the composition is 100%.

In a further aspect the invention relates to a pharmaceutical composition, as described herein, prepared by direct compression or wet granulation. The tablets described herein may be prepared by granulation, in particular wet granulation or direct compression.

In direct compression methods, the drug substance, a compressible filler and other ingredients, if required, are mixed to a homogeneous composition then compressed in a tablet press to produce tablets. All materials used in a direct compression process must be carefully selected with regard to particle size distribution, density, physical form in order to avoid segregation during mixing and to ensure suitable flow and compression properties.

Such properties may also be conferred by granulation, which is a process by which primary particles (powders) are made to adhere to form larger, multiparticulate entities called granules. Granulation normally commences after initial dry mixing of the powdered ingredients so that a fairly uniform distribution of ingredients through the mix is achieved. Granulation methods can be divided into two types, wet granulation methods that utilize a liquid to form the granules and dry methods that do not.

Wet granulation involves mixing the components to be granulated as a dry mix (for example Compound (I), diluent(s), disintegrant(s) and optionally a binder). The dry mix is then massed using a granulating fluid to form granules. Sufficient granulating fluid is added to the dry mix to form granules during the granulation process, for example 10 to 50% by weight, suitably 15 to 25% by weight, of granulating fluid is added to the dry mix during the granulation. The granulating fluid may contain a solvent, which can be removed by drying, and is non-toxic. Suitably however, the granulating fluid is water. The granulating fluid can be used alone or with a binding agent (binder) to ensure particle adhesion in the dry state. Binding agents can be added to the system as a binder solution (as part of the granulating fluid) or as dry material mixed with the primary powder particles (as part of the dry mix). Suitably the granulating liquid is added to the dry powder mix in a manner to provide a substantially uniform liquid content in the mixture, for example by spraying the liquid onto the powder during the granulation. Wet granulators are well known and any suitable granulator may be used to form the wet granules. There are three main types of wet granulator, shear granulators (such as planetary mixers), high shear mixer granulators (such as Vector, Fielder or Diosna) and fluid bed granualtors (such as Aeromatic or Glatt).

Following wet granulation the resulting wet mass may be passed through a course mesh (for example a 9 mm mesh) to remove any large lumps that may have formed during the granulation. The granules are dried to a suitable moisture content, typically less that 2% by weight water, using a suitable drying method such as fluid bed drying. The resulting granules are then optionally milled to give a more homogenous particle size distribution.

In dry granulation methods, primary powder particles are aggregated under pressure (or compaction). There are two main processes: a large tablet (also known as a slug) is produced with a heavy duty tablet press or the powder particles are compressed between two rollers to produce a sheet or 'ribbon' of material (process known as roller compaction). In both cases, the compacted material is milled using a suitable milling technique to produce granular material. The granules can then be compressed in a standard tablet press to produce tablets.

Following granulation the granules might be used in a capsule composition or compressed to form a tablet. Suitably to form a tablet, the granules may be blended with a lubricant and then compressed into tablets. A suitable coating may then be applied to the tablets as described herein.

In one aspect there is provided a pharmaceutical composition, as disclosed herein, prepared by direct compression process that is suitable for oral administration.

In another aspect there is provided a pharmaceutical composition, as disclosed herein, prepared by a wet granulation process that is suitable for oral administration.

In another aspect there is provided a pharmaceutical composition, as disclosed herein, prepared by a dry granulation process that is suitable for oral administration.

In another aspect the invention relates to a pharmaceutical composition obtainable by a wet granulation process comprising Compound (I) with mannitol and/or microcrystalline cellulose.

In this wet granulation process aspect of the invention, the present inventors found that when wet granulation grade mannitol was used, soft, friable tablets were produced. However, when direct compression grade mannitol was used in the wet granulation process described herein, this problem was avoided.

In a further feature of the present invention the present inventors have found that they are able to manufacture satisfactory batches of the preferred composition, using a direct compression grade of mannitol, by both wet granulation and direct compression processes.

"Direct compression grade mannitol", for example Parteck™ M grades of mannitol supplied by Merck Chemicals Ltd., can be produced by a spray drying process causing the mannitol to crystallise in a needle-like microstructure while building up a granular macrostructure. Suitably the average particle size of the direct compression grade mannitol is about 150 to 350 μm, for example 200 to 300 μm. Suitably the direct compression grade mannitol has a bulk density of about 0.45 to 0.50 g/ml. Examples of direct compression grade mannitol prepared by spray drying include Parteck™ M200, Parteck™ M300, Pearlitol™ SD200 or Mannogem™ EZ. In one embodiment of the invention the mannitol is Parteck™ M200.

"Wet granulation grade mannitol" generally has a more granular particle shape than direct compression grade mannitol. Suitably the wet granulation grade mannitol has an average particle size in the range of about 200 to 300 μm. For example Pearlitol™ 160 C supplied by Roquette Freres S. A., comprises cubic crystals having a mean diameter of 160 microns.

In another aspect the invention relates to a pharmaceutical composition obtainable by a wet granulation process comprising Compound (I) with mannitol and/or microcrystalline cellulose wherein direct compression grade mannitol is used in the wet granulation process.

In another aspect the invention relates to a pharmaceutical composition prepared by a wet granulation process comprising Compound (I) with mannitol and/or microcrystalline cellulose wherein direct compression grade mannitol is used in the wet granulation process.

Where the composition comprising Compound (I) with mannitol and/or microcrystalline cellulose is prepared by wet granulation, particularly direct compression grade mannitol is used.

In another aspect the invention relates to a pharmaceutical composition obtainable by a wet granulation process comprising Compound (I), mannitol, microcrystalline cellulose, croscarmellose sodium, a binder and a lubricant.

In another aspect the invention relates to a pharmaceutical composition obtainable by a wet granulation process comprising Compound (I), mannitol, microcrystalline cellulose, croscarmellose sodium, a binder and magnesium stearate.

In another aspect the invention relates to a pharmaceutical composition obtainable by a wet granulation process comprising Compound (I), mannitol, microcrystalline cellulose, croscarmellose sodium, Povidone and a lubricant.

In another aspect the invention relates to a pharmaceutical composition obtainable by a wet granulation process comprising Compound (I), mannitol, microcrystalline cellulose, croscarmellose sodium, Povidone and magnesium stearate.

In another aspect the invention relates to a pharmaceutical composition obtainable by a wet granulation process comprising wet granulation of Compound (I), mannitol, microcrystalline cellulose, croscarmellose sodium and a binder.

In another aspect the invention relates to a pharmaceutical tablet composition obtainable by a wet granulation process comprising:

(i) wet granulation of Compound (I), mannitol, microcrystalline cellulose, croscarmellose sodium and a binder;

(ii) blending the resulting granules with a lubricant; and (iii) compressing the mixture from step (iii) into tablets.

In these embodiments any of the mannitol, microcrystalline cellulose, croscarmellose sodium, binder and lubricants described herein may be used. In a particular embodiment the mannitol is a direct compression grade mannitol such as Parteck M200.

In one aspect the pharmaceutical composition is in a solid dosage form, such as a tablet or capsule. In another aspect the pharmaceutical composition is in the form of a tablet. In a further feature of the invention the composition is in the form of a tablet designed for immediate release. Suitably the immediate release tablet will disintegrate quickly following administration as hereinbefore described. For example, typically represented by in-vitro dissolution times of about 3 to 15 minutes and typically 5 to 8 minutes.

According to a further aspect of the invention there is provided a process for the preparation of a pharmaceutical composition according to the invention comprising mixing compound (I) and the mannitol and/or microcrystalline cellulose and forming the mixture into a unit dosage form such as a tablet or capsule.

In one embodiment of the process, following mixing of compound (I) and the mannitol and/or microcrystalline cellulose (and other optional ingredients as required such as a binder and disintegrant as hereinbefore described) the mixture is granulated and formed into a suitable unit dosage form. Suitable granulation methods are as hereinbefore described. For example the mixture may be wet granulated as described herein. When a binder is used in the composition the binder such as PVP may be incorporated into the mixture prior to granulation as a dry powder. Alternatively, the binder may be added as a solution or dispersion with the wet granulation liquid. Following granulation the granules may be dried and milled and, for example, compressed into a tablet as described hereinbefore. Suitably the composition is provided with a means for protecting Compound (I) from light degradation as described hereinafter. For example, when the composition is in the form of a tablet, the tablet is provided with a light protective coating as described hereinafter.

Accordingly, a further aspect of the invention there is provides a process for the preparation of a pharmaceutical immediate release tablet composition according to the invention comprising:

(i) mixing Compound (I) and the mannitol and/or microcrystalline cellulose;

(ii) granulating the mixture formed in step (i) to form granules;

(iii) optionally milling the granules;

(iv) mixing the granules with a lubricant; and (v) compressing the granules into a tablet.

Additional excipients such as a disintegrant and binder may be included in the mixture in step (i) of the process as described hereinbefore and illustrated in the examples.

In a particular embodiment the granulation step (ii) is a wet granulation as described hereinbefore. When the granulation step (ii) is a wet granulation, the granules are suitably dried prior to milling (if carried out) and subsequent compression into tablets.

In a further embodiment of the process for the preparation of the pharmaceutical immediate release tablet composition, the process further comprises coating the tablets from step (v) with a film coating.

Compound (I) exists in certain crystalline forms. In a particular aspect of the invention, Compound (I) exists in a crystalline form, referred to as Form 1 in the Cambridge crystallographic database. [N-(3-Methoxy-5-methylpyrazin-2-yl)-2-[4-(1,3,4-oxadiazol-2-yl)phenyl]pyridine-3-sulfonamide (ZD4054 Form 1). Acta Crystallographica, Section E: Structure Reports Online (2004), E60(10), o1817-o1819].

In another aspect the invention relates to a pharmaceutical composition as hereinabove defined in which Compound (I) is in a crystalline form.

In yet another aspect the invention relates to a pharmaceutical composition as hereinbefore defined comprising Compound (I) substantially as Form 1.

Substantially as Form 1 means that there is greater than 95% of Form 1 present. In particular there is greater than 96% Form 1. Particularly there is greater than 97% Form 1. In particular there is greater than 98% Form 1. Particularly there is greater than 99% Form 1. In particular there is greater than 99.5% Form 1. Particularly there is greater than 99.8% Form 1.

As mentioned hereinbefore, when the composition is in the form of a tablet, the tablet is suitably coated with a film. We have found that tablet cores coated with a non-pigmented (white) film coating at a level of 2.3% up to about 3.25% relative to the core weight exhibited chemical degradation of Compound (I) following exposure to light. Tablet cores coated with a film coat, including iron oxide pigments, at a level of 3.5% relative to the core weight, did not exhibit significant chemical degradation following exposure to light. Coatings with lower levels of film coatings containing iron oxide pigments may reduce light degradation of Compound (I) compared to the use of a white film coat containing titanium dioxide. In one embodiment of the invention the composition is in the form of a tablet coated with a coating, suitably a film coating, comprising a ferric oxide. In this embodiment the ferric oxide is suitably present at about 0.025 to 0.075% by weight of the tablet, for example about 0.05% by weight of the tablet. The ferric oxide coating may be applied using for example a commercially available coating such as the Opadry™ films supplied by Colorcon Inc.

The formulation of Compound (I) comprising a pigmented (in particular beige) film-coat meets the requirements for a pharmaceutical solid dosage form in late-stage pharmaceutical development in that the formulation is chemically stable in that the levels of light-induced degradation are low.

In one aspect the pharmaceutical composition is a tablet with a coating comprising one or more colouring agents. In another aspect, the pharmaceutical composition is a tablet with a coating comprising three colouring agents. In another aspect, the pharmaceutical composition is a tablet with a coating comprising an iron oxide pigment. In another aspect, the pharmaceutical composition is a tablet with a coating comprising iron oxide pigments. In another aspect, the pharmaceutical composition is a tablet with a coating comprising iron oxide yellow, iron oxide red and iron oxide black. Coatings containing iron oxide pigments are commercially available, for example Opadry Beige (Colorcon 03B27164), which may be applied to the tablet as an aqueous solution or suspension.

In one aspect the pharmaceutical composition is a tablet with a weight of coating between, for example 1 to 10%, such as 2 and 10% by weight of the tablet core weight, for example 3 to 6% by weight of the tablet core weight. In particular, the weight of coating is 3 to 4% by weight of the tablet core weight. In another embodiment the weight of the coating is from about 1 to about 2% by weight of the tablet core weight.

In one aspect the pharmaceutical composition is a tablet with a coating comprising one or more film formers. In another aspect, the pharmaceutical composition is a tablet with a coating comprising one film former. In another aspect, the pharmaceutical composition is a tablet with a coating comprising a water-soluble film-former such as a hydroxypropylmethyl cellulose, for example, Hypromellose 2910 (defined in the PhEur).

In one aspect the pharmaceutical composition is a tablet with a coating comprising one or more opacifiers. In another aspect, the pharmaceutical composition is a tablet with a coating comprising one opacifier. In another aspect, the pharmaceutical composition is a tablet with a coating comprising titanium dioxide.

In one aspect the pharmaceutical composition is a tablet with a coating comprising one or more plasticisers. In another aspect, the pharmaceutical composition is a tablet with a coating comprising one plasticiser. In another aspect, the pharmaceutical composition is a tablet with a coating comprising a polyethylene glycol plasticiser, for example Macrogol 400 (defined in the PhEur).

Tablet coating may be carried out using conventional methods well known in the art, for example coating in a pan coater. The film coat may be applied by spraying an aqueous suspension of the film former, opacifier, plasticiser and colouring agents onto the tablet cores.

In another aspect the invention relates to a pharmaceutical composition comprising a Compound of formula (I) which is a tablet with a coating comprising iron oxide yellow, iron oxide red and iron oxide black.

In another aspect the invention relates to a pharmaceutical composition comprising a Compound of formula (I) which is a tablet with a coating comprising Hypromellose 2910, titanium dioxide, Macrogol 400, iron oxide yellow, iron oxide red and iron oxide black.

In another aspect the invention relates to a tablet comprising a core comprising a Compound of formula (I) with mannitol and/or microcrystalline cellulose and a coating comprising iron oxide yellow, iron oxide red and iron oxide black.

In another aspect the invention relates to a tablet comprising a core comprising a Compound of formula (I) with mannitol and/or microcrystalline cellulose and a coating comprising Hypromellose 2910, titanium dioxide, Macrogol 400, iron oxide yellow, iron oxide red and iron oxide black.

In another aspect, the coating contains from 50 to 75% by weight of film former. In particular, it contains 60.5 to 64.5% by weight of film formers.

In another aspect, the coating contains from 20 to 40% by weight of opacifier. In particular, it contains 27.5 to 31.5% by weight of opacifier.

In another aspect, the coating contains from 5 to 20% by weight of plasticiser. In particular, it contains 4.5 to 8.5% by weight of plasticiser.

In another aspect, the coating contains from 0.5 to 10% by weight of colouring agent. In particular, it contains 1-2% by weight of colouring agent.

In another aspect, the coating contains from 0.025 to 0.075% by weight of iron oxide pigment(s).

In another aspect, the coating contains from 0.025 to 0.075% by weight of iron oxide pigment(s) and from 0.8 to 1.2% by weight of titanium dioxide. For example a coating containing about 0.05% iron oxide and about 1% by weight of titanium dioxide, wherein the weights are % weight relative to the weight of the tablet core to which the coating is applied.

In one aspect the invention relates to a pharmaceutical composition comprising a tablet core and a coating wherein the tablet core comprises:
  Compound (I) in an amount of 4.5 to 8.5% by weight of the core;
  mannitol in an amount of 71.5 to 75.5% by weight of the core; and
  microcrystalline cellulose in an amount of 10.5 to 14.5% by weight of the core;
and wherein the coating on the tablet core comprises:
  iron oxide yellow in an amount of 0.75 to 1.75% by weight of the coating;
  iron oxide red in an amount of 0.1 to 0.6% by weight of the coating; and
  iron oxide black in an amount of 0.06 to 1% by weight of the coating.

In another aspect the invention relates to a pharmaceutical composition comprising a core comprising Compound of formula (I) and a coating comprising:
  a water-soluble film-former such as Hypromellose 2910 in an amount of 60.5 to 64.5% by weight;
  titanium dioxide in an amount of 27.5 to 31.5% by weight;
  a polyethylene glycol plasticiser such as Macrogol 400 in an amount of 4.5 to 8.5% by weight;
  iron oxide yellow in an amount of 0.75 to 1.75% by weight;
  iron oxide red in an amount of 0.1 to 0.6% by weight; and
  iron oxide black in an amount of 0.06 to 1% by weight;
  wherein the weights are % by weight of the coating.

In another aspect the invention relates to a pharmaceutical composition comprising a core comprising a Compound of formula (I) and mannitol with optional microcrystalline cellulose and a coating comprising:
  a water-soluble film-former such as Hypromellose 2910 in an amount of 60.5 to 64.5% by weight;
  titanium dioxide in an amount of 27.5 to 31.5% by weight;
  a polyethylene glycol plasticiser such as Macrogol 400 in an amount of 4.5 to 8.5% by weight;
  iron oxide yellow in an amount of 0.75 to 1.75% by weight;
  iron oxide red in an amount of 0.1 to 0.6% by weight; and
  iron oxide black in an amount of 0.06 to 1% by weight;
  wherein the weights are % by weight of the coating.

In another aspect the invention relates to a pharmaceutical immediate release tablet composition comprising a tablet core and a coating, wherein the tablet core comprises:
  Compound of formula (I) in an amount of 6.0 to 8.0% by weight of the tablet core;
  mannitol in an amount of 72.0 to 75.0% by weight of the tablet core;
  microcrystalline cellulose in an amount of 10.5 to 14.5% by weight of the tablet core;
  croscarmellose sodium in an amount of 2.5 to 4.5% by weight of the tablet core; and
  PVP (for example, Kollidon™ K30 or Plasdone™ K29/32) in an amount of 2.5 to 4.5% by weight of the tablet core; and
  a lubricant (for example magnesium stearate) in an amount of 0.75 to 2.0% by weight (for example 0.8 to 1.75% by weight);
and wherein the coating on the tablet core comprises an iron oxide pigment and wherein the coating is present in an amount of 3 to 6% by weight of the tablet core.

In another aspect the invention relates to a pharmaceutical immediate release tablet composition comprising a tablet core and a coating, wherein the tablet core comprises:
  Compound of formula (I) in an amount of 6.0 to 8.0% by weight of the tablet core;
  mannitol in an amount of 72.0 to 75.0% by weight of the tablet core;
  microcrystalline cellulose in an amount of 10.5 to 14.5% by weight of the tablet core;
  croscarmellose sodium in an amount of 2.5 to 4.5% by weight of the tablet core; and
  PVP (suitably Collidon-K30 or Plasdone K29/32) in an amount of 2.5 to 4.5% by weight of the tablet core; and
  a lubricant (for example magnesium stearate) in an amount of 0.75 to 2.0% by weight (for example 0.8 to 1.75% by weight);
and wherein the coating on the tablet core comprises
  a water-soluble film-former such as Hypromellose 2910 in an amount of 60.5 to 64.5% by weight of the coating;
  titanium dioxide in an amount of 27.5 to 31.5% by weight of the coating;
  a polyethylene glycol plasticiser such as Macrogol 400 in an amount of 4.5 to 8.5% by weight of the coating;
  iron oxide yellow in an amount of 0.75 to 1.75% by weight of the coating;
  iron oxide red in an amount of 0.1 to 0.6% by weight of the coating; and
  iron oxide black in an amount of 0.06 to 1% by weight of the coating.

Suitably in this embodiment the coating is present in an amount of 2.5 to 5% by weight of the tablet core, for example about 3.5% by weight of the tablet core.

In a further aspect of the invention there is provided a pharmaceutical composition which comprises Compound (I) with mannitol and/or microcrystalline cellulose for use as a medicament.

Therefore according to this aspect of the present invention, there is provided a pharmaceutical composition which comprises Compound (I) with mannitol and/or microcrystalline cellulose, for the treatment of cancer in a warm blooded animal such as man.

According to another feature of the present invention, there is provided the use of a pharmaceutical composition which comprises Compound (I) with mannitol and/or microcrystalline cellulose, for the manufacture of a medicament for the treatment of cancer in a warm blooded animal such as man.

According to a further feature of this aspect of the invention there is provided a method of treating cancer which comprises administering an effective amount of a pharmaceutical composition which comprises Compound (I) with mannitol and/or microcrystalline cellulose, to a warm blooded animal such as man.

In another aspect of the invention there is provided a pharmaceutical composition which comprises Compound (I) with mannitol and/or microcrystalline cellulose, for the reduction of abnormal proliferation in a cancerous cell or inducing differentiation of a cancerous cell in a warm blooded animal such as man.

In another aspect of the invention there is provided the use of a pharmaceutical composition which comprises Compound (I) with mannitol and/or microcrystalline cellulose, for the manufacture of a medicament for the reduction of abnormal proliferation in a cancerous cell or inducing differentiation of a cancerous cell in a warm blooded animal such as man.

In another aspect of the invention there is provided a method for reducing abnormal proliferation in a cancerous cell or inducing differentiation of a cancerous cell which comprises administering an effective amount of a pharmaceutical composition which comprises Compound (I) with mannitol and/or microcrystalline cellulose, to a warm blooded animal such as man.

In another aspect of the invention there is provided a pharmaceutical composition which comprises Compound (I) with mannitol and/or microcrystalline cellulose, for inducing apoptosis in a cancerous cell in a warm blooded animal such as man.

In another aspect of the invention there is provided the use of a pharmaceutical composition which comprises Compound (I) with mannitol and/or microcrystalline cellulose, for the manufacture of a medicament for inducing apoptosis in a cancerous cell in a warm blooded animal such as man.

In another aspect of the invention there is provided a method of inducing apoptosis in a cancerous cell which comprises administering an effective amount of a pharmaceutical composition which comprises Compound (I) with mannitol and/or microcrystalline cellulose, to a warm blooded animal such as man.

In another aspect of the invention there is provided a pharmaceutical composition which comprises Compound (I) with mannitol and/or microcrystalline cellulose, for an anti-angiogenic and vascular targeting agent in blood vessels supplying a cancerous cell in a warm blooded animal such as man.

In another aspect of the invention there is provided the use of a pharmaceutical composition which comprises Compound (I) with mannitol and/or microcrystalline cellulose, for the manufacture of a medicament for an anti-angiogenic and vascular targeting agent in blood vessels supplying a cancerous cell in a warm blooded animal such as man.

In another aspect of the invention there is provided a method of providing an anti-angiogenic and vascular targeting agent in blood vessels supplying a cancerous cell which comprises administering an effective amount of a pharmaceutical composition which comprises Compound (I) with mannitol and/or microcrystalline cellulose, to a warm blooded animal such as man.

By the term "vascular targeting agent" it is to be understood that the site of action of a pharmaceutical composition which comprises Compound (I) with mannitol and/or microcrystalline cellulose would be on the vasculature itself rather than the tumour.

In another aspect of the invention there is provided a pharmaceutical composition which comprises Compound (I) with mannitol and/or microcrystalline cellulose, as an anti-angiogenic agent in a warm blooded animal such as man.

In another aspect of the invention there is provided the use of a pharmaceutical composition which comprises Compound (I) with mannitol and/or microcrystalline cellulose, for the manufacture of a medicament for an anti-angiogenic agent in a warm blooded animal such as man.

In another aspect of the invention there is provided a method of providing an anti-angiogenic effect which comprises administering an effective amount of a pharmaceutical composition which comprises Compound (I) with mannitol and/or microcrystalline cellulose, to a warm blooded animal such as man.

In another aspect of the invention there is provided a pharmaceutical composition which comprises Compound (I) with mannitol and/or microcrystalline cellulose, as an inhibitor of bone metastases and an inhibitor of invasion in a warm blooded animal such as man.

In another aspect of the invention there is provided the use of a pharmaceutical composition which comprises Compound (I) with mannitol and/or microcrystalline cellulose, for the manufacture of a medicament for an inhibitor of bone metastases and an inhibitor of invasion in a warm blooded animal such as man.

In another aspect of the invention there is provided a method of inhibiting bone metastases and inhibiting invasion which comprises administering an effective amount of a pharmaceutical composition which comprises Compound (I) with mannitol and/or microcrystalline cellulose, to a warm blooded animal such as man.

In another aspect of the invention there is provided a pharmaceutical composition which comprises Compound (I) with mannitol and/or microcrystalline cellulose, as an inhibitor of bone metastases in a warm blooded animal such as man.

In another aspect of the invention there is provided the use of a pharmaceutical composition which comprises Compound (I) with mannitol and/or microcrystalline cellulose, for the manufacture of a medicament for an inhibitor of bone metastases in a warm blooded animal such as man.

In another aspect of the invention there is provided a method of inhibiting bone metastases which comprises administering an effective amount of a pharmaceutical composition which comprises Compound (I) with mannitol and/or microcrystalline cellulose, to a warm blooded animal such as man.

In another aspect of the invention there is provided a pharmaceutical composition which comprises Compound (I) with mannitol and/or microcrystalline cellulose, for the prevention of bone metastases in a warm blooded animal such as man.

In another aspect of the invention there is provided the use of a pharmaceutical composition which comprises Compound (I) with mannitol and/or microcrystalline cellulose, for the manufacture of a medicament for the prevention of bone metastases in a warm blooded animal such as man.

In another aspect of the invention there is provided a method of preventing bone metastases which comprises administering an effective amount of a pharmaceutical composition which comprises Compound (I) with mannitol and/or microcrystalline cellulose, to a warm blooded animal such as man.

In another aspect of the invention there is provided a pharmaceutical composition which comprises Compound (I) with mannitol and/or microcrystalline cellulose, for the treatment of bone metastases in a warm blooded animal such as man.

In another aspect of the invention there is provided the use of a pharmaceutical composition which comprises Compound (I) with mannitol and/or microcrystalline cellulose, for the manufacture of a medicament for the treatment of bone metastases in a warm blooded animal such as man.

In another aspect of the invention there is provided a method of treating bone metastases which comprises administering an effective amount of a pharmaceutical composition which comprises Compound (I) with mannitol and/or microcrystalline cellulose, to a warm blooded animal such as man.

In a further aspect of the invention, there is provided the inhibition, treatment and/or prevention of bone metastases, as described herein, wherein the bone metastases are as a result of renal, thyroid, lung, breast or prostate cancer.

In another aspect of the invention there is provided a pharmaceutical composition which comprises Compound (I) with mannitol and/or microcrystalline cellulose, for the prevention or treatment of pain associated with elevated endothelin-1 production in a warm blooded animal such as man.

In another aspect of the invention there is provided the use of a pharmaceutical composition which comprises Compound (I) with mannitol and/or microcrystalline cellulose, for the manufacture of a medicament for the prevention or treatment of pain associated with elevated endothelin-1 production in a warm blooded animal such as man.

In another aspect of the invention there is provided a method of treating pain associated with elevated endothelin-1 production which comprises administering an effective amount of a pharmaceutical composition which comprises Compound (I) with mannitol and/or microcrystalline cellulose, to a warm blooded animal such as man.

In another aspect of the invention there is provided a pharmaceutical composition which comprises Compound (I) with mannitol and/or microcrystalline cellulose, for the prevention or treatment of pain in a warm blooded animal such as man.

In another aspect of the invention there is provided the use of a pharmaceutical composition which comprises Compound (I) with mannitol and/or microcrystalline cellulose, for the manufacture of a medicament for the prevention or treatment of pain in a warm blooded animal such as man.

In another aspect of the invention there is provided a method of treating pain which comprises administering an effective amount of a pharmaceutical composition which comprises Compound (I) with mannitol and/or microcrystalline cellulose, to a warm blooded animal such as man.

In another aspect of the invention there is provided a pharmaceutical composition which comprises Compound (I) with mannitol and/or microcrystalline cellulose, for the prevention or treatment of pain associated with stimulation of the $ET_A$ receptor in a warm blooded animal such as man.

In another aspect of the invention there is provided the use of a pharmaceutical composition which comprises Compound (I) with mannitol and/or microcrystalline cellulose, for the manufacture of a medicament for the prevention or treatment of pain associated with stimulation of the $ET_A$ receptor in a warm blooded animal such as man.

In another aspect of the invention there is provided a method of treating pain associated with stimulation of the $ET_A$ receptor which comprises administering an effective amount of a pharmaceutical composition which comprises Compound (I) with mannitol and/or microcrystalline cellulose, to a warm blooded animal such as man.

Where cancer is referred to, particularly it refers to oesophageal cancer, myeloma, hepatocellular, pancreatic, cervical cancer, ewings tumour, neuroblastoma, Kaposis sarcoma, ovarian cancer, breast cancer, colorectal cancer, prostate cancer, bladder cancer, melanoma, lung cancer—non small cell lung cancer (NSCLC), and small cell lung cancer (SCLC)— gastric cancer, head and neck cancer, renal cancer, lymphoma and leukaemia. More particularly it refers to prostate cancer. In addition, more particularly it refers to SCLC, NSCLC, colorectal cancer, ovarian cancer and/or breast cancer. In addition, more particularly it refers to prostate cancer, NSCLC, ovarian cancer, bladder cancer, gastric cancer and/or breast cancer. In addition, more particularly it refers to prostate cancer, NSCLC, ovarian cancer, bladder cancer and/or gastric cancer. In addition, more particularly it refers to prostate cancer, NSCLC, ovarian cancer and/or bladder cancer. In addition, more particularly it refers to SCLC. In addition, more particularly it refers to NSCLC. In addition, more particularly it refers to colorectal cancer. In addition, more particularly it refers to ovarian cancer. In addition, more particularly it refers to breast cancer. Furthermore, more particularly it refers to bladder cancer, oesophageal cancer, gastric cancer, melanoma, cervical cancer and/or renal cancer. In addition it refers to endometrial, liver, stomach, thyroid, rectal and/or brain cancer. In another aspect of the invention, the cancer is not melanoma. In another embodiment of the invention, particularly the cancer is in a metastatic state, and more particularly the cancer produces metastases to the bone. In a further embodiment of the invention, particularly the cancer is in a metastatic state, and more particularly the cancer produces skin metastases. In a further embodiment of the invention, particularly the cancer is in a metastatic state, and more particularly the cancer produces lymphatic metastases. In a further embodiment of the invention, the cancer is in a non-metastatic state.

It is to be understood that when the cancer is in a metastatic state, that a pharmaceutical composition which comprises Compound (I) with mannitol and/or microcrystalline cellulose acts at both the primary tumour site and the metastases by prevention, treatment and inhibition of metastases.

The composition according to the invention may be used alone for the treatment of cancer. Alternatively, the composition according to the invention may also be used in combination with certain other anti-cancer agents for the treatment of cancer as described in WO2004/035057, WO2005/023264 and WO2006/056760. For example, the composition according to the invention may be useful in combination with docetaxel for the treatment of hormone resistant prostate cancer, particularly metastatic hormone resistant prostate cancer, more particularly metastatic hormone resistant prostate cancer in patients who are asymptomatic or mildly symptomatic for pain.

In one aspect of the invention, where pain is referred to, this is pain associated with raised endothelin-1 levels. In another aspect of the invention this is pain associated with stimulation of the $ET_A$ receptor resulting from situations where $ET_B$ down-regulation has occurred leading to abnormal $ET_A$ stimulation and/or elevation of endothelin-1 levels. Particularly this is pain associated with cancer. More particularly it is pain associated with prostate cancer.

Additionally, a pharmaceutical composition which comprises Compound (I) with mannitol and/or microcrystalline cellulose is expected to be useful in the treatment and/or prophylaxis of pain of different origins and causes, including acute as well as chronic pain states. Examples are pain caused by chemical, mechanical, radiation (including sunburn), thermal (including burns), infectious or inflammatory tissue trauma or cancer, postoperative pain, post-partum pain, the pain associated with joint conditions (such as rheumatoid arthritis and osteoarthritis), pain associated with dental conditions (such as dental caries and gingivitis), myofascial and low back pain, pain associated with bone disorders (such as osteoporosis, hypercalcaemia of malignancy and Paget's disease) and the pain associated with sports injuries and sprains.

Also neuropathic pain conditions of central or peripheral origin could be treated or prevented with a pharmaceutical composition which comprises Compound (I) with mannitol and/or microcrystalline cellulose. Examples of these pain conditions are pain associated with trigeminal neuralgia, pain associated with postherpetic neuralgia (PHN), pain associated with diabetic mono/poly neuropathy, pain associated with nerve trauma, pain associated with spinal cord injury, pain associated with central post stroke, pain associated with multiple sclerosis and pain associated with Parkinson's disease.

Other pain states of visceral origin such as caused by ulcer, dysmenorrhea, endometriosis, irritable bowel syndrome, dyspepsia etc. could also be treated or prevented with a pharmaceutical composition which comprises Compound (I) with mannitol and/or microcrystalline cellulose.

A further aspect of the invention is to use a pharmaceutical composition which comprises Compound (I) with mannitol and/or microcrystalline cellulose for oral treatment of neuropathic or central pain states.

It is to be understood that the uses and methods of treatment described herein may use any of the compositions comprising Compound (I) with mannitol and/or microcrystalline cellulose described herein.

| | General Experimental Materials | | | |
|---|---|---|---|---|
| Material | Pharmacopoeia | Function | Example | Supplier |
| Mannitol | PhEur[1], USP-NF[2], JP[3] | Filler (direct compression) | Parteck ™ M200 EMPROVE ® | Merck Chemicals Ltd. (UK) |
| | | Filler (wet granulation) | Pearlitol ™ 160 C | Roquette Freres S.A. (France) |
| Cellulose, microcrystalline | Ph Eur, USP-NF, JP | Filler | Avicel ® PH-101 | FMC Biopolymer (Ireland) |
| Magnesium carbonate, heavy | PhEur, USP-NF, JP | Filler | | L.M. Loveridge Ltd. (UK) |
| Calcium phosphate dihydrate | USP-NF | Filler | Calipharm D | Innophos (USA) |
| Povidone | PhEur, USP-NF, JP | Binder | Plasdone ™ K29/32 | ISP Technologies, Inc. (USA) |
| Croscarmellose sodium | PhEur, USP-NF, JP | Disintegrant | AcDiSol ™ SD-711 | FMC Biopolymer (Ireland) |
| Crospovidone | PhEur, USP-NF | Disintegrant | Polyplasdone ® | International Specialty Products (USA) |
| Magnesium stearate | PhEur, USP-NF, JP | Lubricant | Magnesium Stearate NF Non-Bovine HyQual ® | Mallinckrodt Inc. (USA) |
| Hypromellose | PhEur, USP-NF, JP | Film former | Opadry ™ Beige[4] | Colorcon Limited (UK) |
| Titanium dioxide | PhEur, USP | Opacifier | | |
| Iron oxide, black ($Fe_3O_4$, magnetite, CAS#1317-61-9) | | Pigment | | |
| Iron oxide, red ($Fe_2O_3$, haematite, CAS#1309-37-1) | | | | |
| Iron oxide, yellow ($Fe(OH)_3$, goethite, CAS#20344-49-4) | | | | |
| Polyethylene glycol | PhEur (Macrogols), USP-NF, JP (Macrogol) | Plasticiser | | |

[1]PhEur: European Pharmacopoeia 5th Edition (Directorate for the Quality of Medicines of the Council of Europe) 2007.
[2]USP-NF: United States Pharmacopeia 30/National Formulary 25 (The United States Pharmacopeia Convention) 2007.
[3]JP: Japanese Pharmacopeia 15th Edition, English Version (Society of Japanese Pharmacopoeia) 2006.
[4]The film-coat may be supplied as a proprietary concentrate (eg, Opadry, product identifier 03B27164) or powder mixture that requires reconstitution in purified water, prior to application as an aqueous suspension to the tablet cores.

Hardness

Hardness testing was carried out using a Schleuniger Hardness Tester Model 6D or equivalent, in accordance with the procedure specified in the European Pharmacopoeia (Resistance to crushing of tablets), except that the number of tablets tested was as specified in the table. The hardness of each tablet was measured along its diameter. The average 'hardness' is reported in kiloponds (kp).

Disintegration Time

Disintegration time was measured out in accordance with the procedure specified in the European Pharmacopoeia, without a disc and using water as the medium. Disintegration time is reported in minutes (min.).

Compound (I) Assay and Impurities

The Compound (I), Compound (I) formyl hydrazide, and total impurities contents were determined using High Performance Liquid Chromatography HPLC. 10 µL sample was injected into a mobile phase comprising water/acetonitrile/formic acid in the ratios 900:100:2 (Eluent A)/400:600:2 (Eluent B), as defined by the gradient program in Table 1 below.

The solution for the impurities determination is prepared by extraction from a known weight of finely ground tablets using 1:1 acetonitrile:water as extraction solvent, followed by filtration through a 0.45 micron PTFE filter, such that the target concentration of Compound (I) in the test solution is 0.25 mg/mL.

TABLE 1

Gradient programme - Compound (I) assay and impurities

|  | Time (mins) | % A | % B |
|---|---|---|---|
| Gradient programme | 0 | 100 | 0 |
|  | 50 | 0 | 100 |
|  | 51 | 100 | 0 |
|  | 60 | 100 | 0 |

The mobile phase starts as 100% eluent A at time zero, then the composition is modified by increasing the proportion of eluent B gradually and linearly such that after 50 minutes the mobile phase comprises 100% eluent B. This composition is maintained for 1 minute, then reverts to 100% eluent A in order to re-equilibrate the column.

Separation of impurities was performed using a column 15 cm long×4.6 mm internal diameter packed with Waters Symmetry C8 stationary phase having 3.5 µm particle size. The mobile phase flow rate was 1.0 mL/minute, temperature was controlled at 25° C., and impurity concentration was determined by comparison of absorbance at 254 nm, measured using a variable wavelength uv detector, with that of an external Compound (I) reference standard.

Dissolution

Dissolution was determined according to the general procedure of the United States Pharmacopoeia (USP) using Apparatus 2 with 900 mL of 0.1 M Phosphate buffer at pH 7.8 as dissolution medium and a stirrer speed of 50 rpm. At 15, 30 and 45 minutes, 10 ml of dissolution media was withdrawn and filtered through a 0.45 µm PTFE filter, discarding the first 2 ml of filtrate. The amount of Compound (I) in solution was measured using an HPLC procedure similar to that described above, except that the method was operated under isocratic conditions using as mobile phase water: acetonitrile orthophosphoric acid in the ratio 700:300:2. The sample volume was 50 µL, the stationary phase was Jones Chromatography Genesis C18, the mobile phase flow rate was 1.5 mL/minute, temperature was controlled at 40° C., and the measurement wavelength was 224 nm.

Friability

Twenty tablets were accurately weighed and placed in a rotating drum (Copley TA-10 or equivalent). The drum was rotated 100 times and the tablets removed. Loose dust was removed from the tablets and the tablets re-weighed. The friability is expressed as the loss of mass and it is calculated as a percentage of the initial mass.

EXPERIMENTAL AND RESULTS

In the following results and tables where "ND" is stated, it is to be understood that this refers to a value lower than the detection limits of the methods used.

Example 1

Compound (I) Forced Degradation Study

The stability of Compound (I) drug substance at an initial concentration of 0.5 mg/mL in solution in aqueous buffers, in the dark at room and elevated temperature over a period of 24 hours, as shown in Table 2, and exposed to light at room temperature (RT) over a period of 2 hours, as shown in Table 3, was investigated in a forced degradation study. The results are summarised in Tables 2 and 3. "ND" in Tables 2 and 3 refers to "not determined"

TABLE 2

Compound (I) forced degradation study (0.5 mg/mL solutions) (solutions protected from light)

|  | pH 1.2 | | pH 3.0 | | pH 7.2 | | pH 11.0 | |
|---|---|---|---|---|---|---|---|---|
|  | RT | 37° C. | RT | 37° C. | RT | 37° C. | RT | 37° C. |
| Compound (I), % w/w (initial/24 hours) | 97.57/ 23.04 | 96.69/ 0.89 | 99.45/ 84.70 | 99.43/ 96.56 | 99.14/ 99.45 | 98.73/ 99.17 | 98.68/ 94.21 | 99.17/ 94.50 |
| Compound (I) formyl hydrazide, % w/w (initial/24 hours) | 1.99/ 59.83 | 1.58/ 32.16 | ND/ 1.66 | ND/ 3.09 | ND/ ND | ND/ ND | 0.07/ 1.35 | ND/ 4.16 |
| Compound (I) hydrazide, % w/w (initial/24 hours) | ND/ 13.87 | ND/ 47.34 | ND/ <0.05 | ND/ ND | ND/ <0.05 | ND/ <0.05 | ND/ ND | ND/ <0.05 |

TABLE 3

| | Compound (I) forced degradation study (solutions exposed to light at room temperature) | | | |
|---|---|---|---|---|
| | pH 1.2 | pH 3.0 | pH 7.2 | pH 11.0 |
| Compound (I), % w/w (initial/24 hours) | 98.82/82.33 | 99.39/95.76 | 98.78/97.04 | 99.91/98.66 |
| Compound (I) formyl hydrazide, % w/w (initial/24 hours) | 1.39/16.35 | 0.05/0.30 | ND/ND | <0.05/0.15 |
| Compound (I) hydrazide, % w/w (initial/24 hours) | ND/0.32 | ND/ND | ND/ND | ND/ND |

Example 2

Stability Study for Lactose-based Tablets

Compound (I) lactose-based tablets were manufactured using wet granulation, compression and film coating processes, using the formulations shown in Table 4. The powdered ingredients (other than the binder and lubricant) were charged to a suitable mixer and mixed to produce a uniform distribution of drug substance (Compound (I)). An aqueous binder solution (povidone) was prepared and added to the powders with further mixing until a suitable wet mass was formed. The wet mass was passed through a screen (mesh size 9 mm) and the resultant granules dried to an appropriate moisture content (less than 2% by weight). The lubricant was added to the dry granules, which were then passed through a suitable screen (mesh size 1.4 mm) prior to blending. The blended granules were compressed into tablet cores using tableting equipment (using a rotary press to give tablets of the required hardness, disintegration and appearance). The compressed cores were then coated with an aqueous suspension of film coating components using a perforated drum coater (for example an O'hara coater).

TABLE 4

| Active tablet (10 mg, lactose monohydrate filler) | | | |
|---|---|---|---|
| Ingredient | mg/tablet | % of core weight | Function |
| Tablet core | | | |
| Compound (I) | 10.0 | 4.00 | Drug substance |
| Lactose monohydrate | 222.5 | 89.00 | Filler |
| Croscarmellose sodium | 10.0 | 4.00 | Disintegrant |
| Povidone K29/32 | 5.0 | 2.00 | Binder |
| Magnesium stearate | 2.5 | 1.00 | Lubricant |
| Core tablet weight | 250.0 | | |
| Tablet coating | | % of coating weight | |
| Hypromellose 606 | 3.75 | 65.22 | Film-former |
| Polyethylene glycol 300 | 0.75 | 13.04 | Plasticiser |
| Titanium dioxide | 1.25 | 21.74 | Opacifier |
| | | % of core weight | |
| Nominal coating weight | 5.75 | 2.30 | |

These tablets were tested for Compound (I) assay and impurities immediately after preparation and after periods of storage under various conditions of temperature and relative humidity (RH), as shown in Table 5.

TABLE 5

| Stability data summary - lactose tablets | | | | | | |
|---|---|---|---|---|---|---|
| | | Initial | 25° C./60% RH (36 months) | 40° C./75% RH (12 months) | 50° C. (6 months) | Light (10 days) |
| 10 mg tablets (Table 4) | Compound (I) (mg/tablet) | 9.8 | 9.9 | 9.8 | 9.9 | 9.9 |
| | Compound (I) formyl hydrazide (%) | <0.05 | 0.13 | 0.19 | 0.09 | <0.05 |
| | Total impurities (%) | <0.05 | 0.13 | 0.19 | 0.09 | 0.38 |

Example 3

Excipient Compatibility Study

Possible materials were evaluated in accordance with the experimental design matrix shown in Table 6.

TABLE 6

Experimental Design Matrix

| Exp | Filler (A) | Disintegrant (B) | Binder (C) |
|---|---|---|---|
| 1 | Magnesium carbonate, heavy | Crospovidone | HPMC |
| 2 | Magnesium carbonate, heavy | Croscarmellose sodium | Povidone |
| 3 | Calcium phosphate dihydrate | Crospovidone | HPMC |
| 4 | Calcium phosphate dihydrate | Croscarmellose sodium | Povidone |
| 5 | Microcrystalline cellulose | Croscarmellose sodium | HPMC |
| 6 | Microcrystalline cellulose | Crospovidone | Povidone |
| 7 | Mannitol (direct compression) | Croscarmellose sodium | HPMC |
| 8 | Mannitol (direct compression) | Crospovidone | Povidone |

For each experiment, the following formulation was used:

TABLE 7

Tablet composition used in the excipient compatibility study

| Ingredient | mg/tablet | % w/w | Function |
|---|---|---|---|
| Compound (I) | 10.00 | 6.67 | Drug substance |
| (See Table 6) | 129.50 | 86.33 | Filler |
| (See Table 6) | 6.00 | 4.00 | Disintegrant |
| (See Table 6) | 3.00 | 2.00 | Binder |
| Magnesium stearate | 1.50 | 1.00 | Lubricant |
| Core tablet weight | 150.00 | | |

Tablet cores for this study were manufactured using wet granulation, compression processes using an analogous wet granulation method to that described in Example 2. These tablet cores were tested for Compound (I) assay/impurities and dissolution, immediately after preparation and after periods of storage under various conditions of temperature and relative humidity (RH), as shown in Table 8.

TABLE 8

Summary of results from the excipient compatibility study

| Ex | | Initial | 70° C. 7 days | 70° C. 14 days | 70° C./80% RH 7 days | 70° C./80% RH 14 days | Light |
|---|---|---|---|---|---|---|---|
| 1 | Dissolution (%) | 100.99 | 98.10 | 94.01 | 91.80 | 90.00 | 98.10 |
|   | Total Impurities (%) | 0.215 | 2.877 | 3.798 | 3.580 | 5.030 | 3.174 |
| 2 | Dissolution (%) | 89.58 | 94.57 | 83.00 | 22.82 | 20.36 | 94.57 |
|   | Total Impurities (%) | 0.227 | 2.639 | 3.522 | 2.028 | 3.362 | 2.996 |
| 3 | Dissolution (%) | 54.64 | 54.43 | 52.70 | 70.45 | 50.81 | 54.43 |
|   | Total Impurities (%) | 0.107 | 0.499 | 0.761 | 0.261 | 0.328 | 2.172 |
| 4 | Dissolution (%) | 66.38 | 58.41 | 65.45 | 51.88 | 46.54 | 58.41 |
|   | Total Impurities (%) | 0.096 | 0.426 | 0.543 | 0.165 | 0.320 | 2.693 |
| 5 | Dissolution (%) | 96.54 | 94.79 | 98.30 | 94.86 | 96.47 | 94.79 |
|   | Total Impurities (%) | 0.078 | 0.187 | 0.238 | 0.115 | 0.139 | 1.731 |
| 6 | Dissolution (%) | 98.79 | 96.21 | 98.77 | 96.29 | 98.05 | 96.21 |
|   | Total Impurities (%) | 0.077 | 0.097 | 0.134 | 0.163 | 0.206 | 1.904 |
| 7 | Dissolution (%) | 94.97 | 94.61 | 94.81 | 69.23 | 68.48 | 94.61 |
|   | Total Impurities (%) | 0.141 | 0.113 | 0.143 | 0.121 | 0.120 | 1.145 |
| 8 | Dissolution (%) | 96.79 | 101.79 | 100.06 | 98.66 | 99.58 | 101.79 |
|   | Total Impurities (%) | 0.078 | 0.078 | 0.099 | 0.168 | 0.201 | 1.246 |

NB: Table quotes dissolution (% release) measured at 45 mins.

Example 4

Mannitol/Microcrystalline Cellulose Formulations

Placebo tablet cores containing (i) mannitol and (ii) mannitol and microcrystalline cellulose were investigated for their tensile strength and disintegration time.

Example 4i

Placebo Tablet Cores Manufactured Using Mannitol as Filler

TABLE 9

Placebo tablet formulation (mannitol filler)

| Ingredient | mg/tablet | % w/w | Function |
|---|---|---|---|
| Mannitol | 266.63 | 91.0 | Filler |
| Croscarmellose sodium | 11.72 | 4.0 | Disintegrant |
| Povidone K29/32 | 11.72 | 4.0 | Binder |
| Magnesium stearate | 2.93 | 1.0 | Lubricant |
| Core tablet weight | 293 | | |

The formulation described in Example 4i was prepared by a wet granulation and compression process, using an analogous method to that described in Example 2 except that the binder was added as a powder at the dry mix stage, and water was used as the granulating medium at the wet mix stage.

Example 4ii

Placebo Tablet Cores Manufactured Using Mannitol and Microcrystalline Cellulose as Filler

TABLE 10

Placebo tablet (mannitol/microcrystalline cellulose filler)

| Ingredient | mg/tablet | % w/w | Function |
|---|---|---|---|
| Mannitol | 120.12 | 45.5 | Filler |
| Microcrystalline cellulose | 120.12 | 45.5 | Filler |
| Croscarmellose sodium | 10.56 | 4.0 | Disintegrant |
| Povidone K29/32 | 10.56 | 4.0 | Binder |
| Magnesium stearate | 2.64 | 1.0 | Lubricant |
| Core tablet weight | 264.00 | | |

The formulation described in Example 4ii was prepared by wet granulation and compression processes analogous to those described in Example 2, except that the binder was added as a powder at the dry mix stage, and water was used as the granulating medium at the wet mix stage.

Tablet cores from Examples 4i and 4ii were tested for hardness and disintegration time immediately after manufacture and after 4 weeks storage under various conditions of temperature and RH, as shown in Table 11.

TABLE 11

Stability data summary for Placebo Tablets from Examples i (tablet described in Table 9) and Example ii (tablet described in Table 10)

| | Hardness (kp) | | | Disintegration Time (min.) | | |
|---|---|---|---|---|---|---|
| | Initial | 25° C./60% RH | 40° C./75% RH | Initial | 25° C./60% RH | 40° C./75% RH |
| Example 4i (mean of 10 tablets) | 7.056 | 8.484 | 17.16 | 1.76 | 2.18 | 6.25 |
| Example 4ii (mean of 10 tablets) | 8.005 | 7.750 | 6.954 | 0.63 | 0.68 | 0.79 |

Example 5

Formulation

A 10 mg tablet formulation is shown in Table 12.

TABLE 12

Active tablet (10 mg, mannitol/microcrystalline cellulose filler)

| Ingredient | mg/tablet | % of core weight | Function |
|---|---|---|---|
| Tablet core | | | |
| Compound (I) | 10.000 | 6.67 | Drug substance |
| Mannitol | 110.750 | 73.83 | Filler |
| Microcrystalline cellulose | 18.750 | 12.50 | Filler |
| Croscarmellose sodium | 4.500 | 3.00 | Disintegrant |
| Povidone K29/32 | 4.500 | 3.00 | Binder |
| Magnesium stearate | 1.500 | 1.00 | Lubricant |
| Core tablet weight | 150.000 | | |

| Tablet coating | | % of coating weight | |
|---|---|---|---|
| Hypromellose 2910 | 3.281 | 62.50 | Film former |
| Titanium dioxide | 1.563 | 29.77 | Opacifier |
| Polyethylene glycol 400 | 0.328 | 6.25 | Plasticiser |
| Iron oxide yellow | 0.059 | 1.12 | Colouring agent |
| Iron oxide red | 0.014 | 0.27 | Colouring agent |
| Iron oxide black | 0.004 | 0.08 | Colouring agent |

| | | % of core weight | |
|---|---|---|---|
| Nominal coating weight | 5.250 | 3.50 | |

The tablets may be prepared using, for example, the following wet granulation process:

Compound (I) (1.334 kg), mannitol (Partek™ M200, Merck, 14.76 kg), microcrystalline cellulose (Avicel™ PH101, FMC, 2.5 kg), croscarmellose sodium (Ac-Di-Sol™, FMC, 600 g) and poyvinylpyrrolidinone (Plasdone™ K29/32, ISP, 600 g) are mixed together in a Vector GMX75 high shear blender. Water (4.5 kg, addition rate of 1.2 kg/minute) is sprayed into the mixture and the mixture granulated for about 5 minutes. The granules are dried in an O'Hara 30/60 fluid bed dryer (inlet air temperature 70° C., air flow rate sufficient to fluidise the granule bed) to a moisture content of <2% w/w and the dried granules milled using a Quadro Co mil 194 (screen mesh 0.062 inches (1.6 mm), 400 rpm).

Four of the above portions are combined and 800 g magnesium stearate added. The 80 kg batch is transferred to a Pharmatech BV400 blender and the mixture blended. The mixture is then compressed into tablets (150 mg compression weight, plain, round, bi-convex 7 mm diameter) using an IMA Kilian Synthesis 500 tablet press (80,000 tablets per hour, 7.5 kN compression force). The tablets are then coated using a Manesty Premier 200 coater with Opadry Beige (Colorcon 03B27164, 315 g/kg aqueous solution). The total coating solution applied is equivalent to 35 g/kg of Opadry per mass of tablet cores.

The tablets may also be prepared using aqueous PVP as the granulation liquid instead of water in the process described above.

A 15 mg tablet formulation is shown in Table 12A.

TABLE 12A

| Ingredient | mg/tablet | % of core weight | Function |
|---|---|---|---|
| Tablet core | | | |
| Compound (I) | 15.000 | 6.67 | Drug substance |
| Mannitol | 166.125 | 73.83 | Filler |
| Microcrystalline cellulose | 28.125 | 12.50 | Filler |
| Croscarmellose sodium | 6.750 | 3.00 | Disintegrant |
| Povidone K29/32 | 6.750 | 3.00 | Binder |
| Magnesium stearate | 2.250 | 1.00 | Lubricant |
| Core tablet weight | 225.000 | | |

| Tablet coating | | % of coating weight | |
|---|---|---|---|
| Hypromellose 2910 | 4.922 | 62.50 | Film former |
| Titanium dioxide | 2.345 | 29.77 | Opacifier |
| Polyethylene glycol 400 | 0.492 | 6.25 | Plasticiser |
| Iron oxide yellow | 0.089 | 1.12 | Colouring agent |
| Iron oxide red | 0.022 | 0.27 | Colouring agent |
| Iron oxide black | 0.006 | 0.08 | Colouring agent |

| | | % of core weight | |
|---|---|---|---|
| Nominal coating weight | 7.876 | 3.50 | |

The 15 mg tablets may be prepared using an analogous method to that described for the preparation of the 10 mg tablets shown in Table 12.

A stability study was carried out on batches of beige film-coated 10 mg tablets prepared as described in Table 12; and the results are summarised in Table 13.

TABLE 13

Stability data summary for mannitol/microcrystalline cellulose formulations

| | | Initial | 25° C./60% RH (12 months) | 40° C./75% RH (12 months) | 50° C. (6 months) | Light (10 days) |
|---|---|---|---|---|---|---|
| 10 mg tablets (Table 12) | Compound (I) (mg/tablet) | 9.5 | 9.6 | 9.8 | 9.5 | 9.8 |
| | Compound (I) formyl hydrazide (%) | <0.05 | ND | 0.10 | <0.05 | <0.05 |
| | Total impurities (%) | <0.05 | ND | 0.10 | <0.05 | <0.05 |
| | Dissolution (% release after 45 minutes) | 101 | 94 | 93 | 97 | 101 |
| | Hardness (mean of 15 tablets, kp) | 15.53 | 14.13 | 16.37 | N/A | N/A |
| | Disintegration time (min.) | 7.58 | 6.85 | 8.85 | N/A | N/A |

Example 6

Comparison of Mannitol Grades

Mannitol is available in two grades for use as a pharmaceutical excipient in tablet manufacture: a wet granulation grade, for example Pearlitol® C supplied by Roquette Freres S. A., and a direct compression grade, such as Parteck M™ supplied by Merck Chemicals Ltd. Three batches of tablet cores, as described in Table 12, were processed using the mannitol grade and manufacturing process as indicated in Table 14.

TABLE 14

Batches manufactured in the comparison of mannitol grades

| | Mannitol Grade | Manufacturing Process |
|---|---|---|
| Batch 1 | Wet Granulation | Wet Granulation |
| Batch 2 | Direct Compression | Wet Granulation |
| Batch 3 | Direct Compression | Direct Compression |

The direct compression tablets were manufactured using a direct compression process. The Compound (I) and the mannitol were sieved into a bowl and then mixed together in a planetary mixer for 10 minutes. The remaining mannitol, the microcrystalline cellulose, the croscarmellose sodium and the Povidone K29/32 were then added to the bowl and the mixture was mixed for a further 10 minutes. The magnesium stearate was then added through a sieve and the mixture was mixed for a further 5 minutes. The resultant mixture was then compressed into tablet cores, using a target compression force of 5.0KN.

The tablets prepared using wet granulation were prepared using an analogous method to that described in Example 2.

The physical characteristics of the three batches of tablet cores were determined and dissolution was measured using the procedure described previously, except that the dissolution medium was 500 ML pH 1.4 sodium chloride/hydrochloric acid buffer (0.1 M) and the stirrer speed was 75 rpm. The results are summarised in Table 15.

TABLE 15

Physical characteristics of the batches in the comparison of mannitol grades

| | Hardness (kp) | Thickness (mm) | Dissolution (% release after 45 minutes) | Friability (%) |
|---|---|---|---|---|
| Batch 1 | 2.96 | 3.77 | N/A | 0.30 |
| Batch 2 | 5.40 | 3.95 | 89.7 | 0.03 |
| Batch 3 | 8.89 | 3.92 | 87.3 | 0.03 |

Example 7

Mannitol/Microcrystalline Cellulose Formulations Containing Compound (I)

Two experimental batches were manufactured comprising Compound (I) and magnesium stearate in the same proportions as in the final formulation (Table 12), with an increased binder and disintegrant content (from 3% to 5%), without microcrystalline cellulose (Table 16) and with microcrystalline cellulose content increased from 12.5% to 25% (Table 17). The resulting tablet cores were tested for hardness immediately after manufacture and after storage for 16 months at 25° C./65% RH (Table 18).

TABLE 16

Formulation of Compound (I) with Mannitol filler

| Ingredient | mg/tablet | % w/w | Function |
|---|---|---|---|
| Tablet core | | | |
| Compound (I) | 10.000 | 6.67 | Drug substance |
| Mannitol | 123.5 | 82.33 | Filler |
| Croscarmellose sodium | 7.500 | 5.00 | Disintegrant |
| Povidone K29/32 | 7.500 | 5.00 | Binder |
| Magnesium stearate | 1.500 | 1.00 | Lubricant |
| Core tablet weight | 150.000 | | |

TABLE 17

Formulation of Compound (I) with mixed mannitol/microcrystalline cellulose filler

| Ingredient | mg/tablet | % w/w | Function |
|---|---|---|---|
| Tablet core | | | |
| Compound (I) | 10.000 | 6.67 | Drug substance |
| Mannitol | 86.000 | 57.33 | Filler |
| Microcrystalline cellulose | 37.500 | 25.00 | Filler |
| Croscarmellose sodium | 7.500 | 5.00 | Disintegrant |
| Povidone K29/32 | 7.500 | 5.00 | Binder |
| Magnesium stearate | 1.500 | 1.00 | Lubricant |
| Core tablet weight | 150.000 | | |

TABLE 18

Hardness data (KP)

| | Time of Manufacture | 65 weeks storage (room temperature) |
|---|---|---|
| Mannitol formulation (Table 16) | 11.6 | 7.43 |
| Mannitol/microcrystalline cellulose formulation (Table 17) | 9.8 | 7.52 |

The invention claimed is:

1. A pharmaceutical composition which comprises N-(3-methoxy-5-methylpyrazin-2-yl)-2-(4-[1,3,4-oxadiazol-2-yl]pheny)pyridine-3-sulphonamide with mannitol and microcrystalline cellulose.

2. The pharmaceutical composition of claim 1 wherein the mannitol is present in an amount of 65 to 75% by weight and the microcrystalline cellulose is present in an amount of 10 to 15% by weight.

3. The pharmaceutical composition of claim 1 additionally comprising one or more binders.

4. The pharmaceutical composition of claim 3 wherein the binder is Povidone.

5. The pharmaceutical composition of claim 1 additionally comprising one or more disintegrants.

6. The pharmaceutical composition of claim 5 wherein the disintegrant is croscarmellose sodium.

7. The pharmaceutical composition of claim 1 additionally comprising one or more lubricants.

8. The pharmaceutical composition of claim 1 additionally comprising one or more binders, one or more disintegrants and one or more lubricants.

9. The pharmaceutical composition of claim 1 wherein the N-(3-methoxy-5-methylpyrazin-2-yl)-2-(4-[1,3,4-oxadiazol-2-yl]phenyl)pyridine-3-sulphonamide is present in an amount of 2 to 20% by weight.

10. A pharmaceutical composition comprising:
N-(3-methoxy-5-methylpyrazin-2-yl)-2-(4-[1,3,4-oxadiazol-2-yl]phenyl)pyridine-3-sulphonamide in an amount of 4.5 to 8.5% by weight;
mannitol in an amount of 71 to 76% by weight;
microcrystalline cellulose in an amount of 10.5 to 14.5% by weight;
croscarmellose sodium in an amount of 2.5 to 3.5% by weight;
povidone in an amount of 2.5 to 3.5% by weight; and
magnesium stearate in an amount of 0.75 to 2.0% by weight.

11. The pharmaceutical composition of claim 1 with a coating comprising an iron oxide pigment.

12. The pharmaceutical composition of claim 1 wherein the composition is a tablet.

13. The pharmaceutical composition of claim 12 wherein the tablet is an immediate release tablet.

14. A method of treating cancer which comprises administering an effective amount of a pharmaceutical composition of claim 1, to a warm blooded animal.

15. The method of claim 14, wherein the cancer is selected from prostate cancer, non-small cell lung cancer, ovarian cancer, bladder cancer and gastric cancer.

16. The method of claim 14, wherein the cancer is prostate cancer.

17. A method of treating cardiovascular diseases which comprises administering an effective amount of a pharmaceutical composition of claim 1, to a warm blooded animal.

* * * * *